US007834029B2

(12) United States Patent
Beight et al.

(10) Patent No.: US 7,834,029 B2
(45) **Date of Patent: *Nov. 16, 2010**

(54) QUINOLINYL-PYRROLOPYRAZOLES

(75) Inventors: Douglas Wade Beight, Frankfort, IN (US); Jason Scott Sawyer, Indianapolis, IN (US); Jonathan Michael Yingling, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 686 days.

This patent is subject to a terminal disclaimer.

(21) Appl. No.: 11/782,659

(22) Filed: Jul. 25, 2007

(65) Prior Publication Data

US 2008/0027102 A1 Jan. 31, 2008

Related U.S. Application Data

(63) Continuation of application No. 10/531,237, filed as application No. PCT/US03/32747 on Nov. 10, 2003, now Pat. No. 7,265,225.

(60) Provisional application No. 60/428,893, filed on Nov. 22, 2002.

(51) Int. Cl.
*A61K 31/04* (2006.01)
*C07D 215/38* (2006.01)

(52) U.S. Cl. ........................ 514/312; 546/157; 546/167

(58) Field of Classification Search ................. 514/314; 546/157, 167
See application file for complete search history.

(56) References Cited

U.S. PATENT DOCUMENTS

2004/0106604 A1 6/2004 Beight et al.

FOREIGN PATENT DOCUMENTS

| | | |
|---|---|---|
| EP | 0 531 901 | 3/1993 |
| WO | WO 02 094833 | 11/2002 |
| WO | WO 2004/048383 | 6/2004 |

OTHER PUBLICATIONS

Edlund, Molecular Biology of the Cell, vol. 14, pp. 529-544, Feb. 2003.*
Butta, Cancer Research, vol. 52, pp. 4261-4264, Aug. 1992.
Anscher, et al. (1993) N. Engl. J. Med. 328: 1592-1598.
Arteaga, et al. (1993) J. Clin. Invest. 92:2569-2576.
Arteaga, et al. (1993) Cell Growth and Differ. 4:193-201.
Dickson, et al. (1987) Proc. Natl. Acad. Sci. USA 84:837-841.
Daly, et al. (1990) J. Cell Biochem. 43:199-211.
King, et al. (1989) J. Steroid Biochem. 34:133-138.
Welch, et al. (1990) Proc. Natl. Acad. Sci. USA 87:7678-7682.
Walker, et al. (1992) Eur. J. Cancer 28:641-644.

* cited by examiner

*Primary Examiner*—D. Margaret Seaman
(74) *Attorney, Agent, or Firm*—Elizabeth A. McGraw; Danica Hostettler; Tina M. Tucker

(57) ABSTRACT

A compound according to formula II and the pharmaceutically acceptable salts thereof and the method of treating cancer in a patient in need thereof by administration of said compound.

Formula II

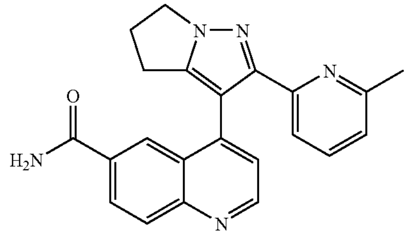

1 Claim, No Drawings

QUINOLINYL-PYRROLOPYRAZOLES

This application is a continuation of U.S. patent application Ser. No. 10/531,237, filed Apr. 13, 2005 now U.S. Pat. No. 7,265,225, which is a 35 U.S.C. 371 National Stage Filing of PCT/US2003/032747 filed Nov. 10, 2003, which claims priority to U.S. Provisional Application No. 60/428,893, filed Nov. 22, 2002.

The invention relates to new quionolinyl-pyrazole compounds and their use as pharmaceutical agents, in particular their use as TGF-beta signal transduction inhibitors.

BACKGROUND OF THE INVENTION

The transforming growth factor-beta (TGF-beta) ("TGF-β") polypeptides influence growth, differentiation, and gene expression in many cell types. The first polypeptide of this family that was characterized, TGF-β1, has two identical 112 amino acid subunits that are covalently linked. TGF-β1 is a highly conserved protein with only a single amino acid difference distinguishing humans from mice. There are two other members of the TGF-β gene family that are expressed in mammals. TGF-β2 is 71% homologous to TGF-β1 (de Martin, et al. (1987) EMBO J. 6:3673-3677), whereas TGF-β3 is 80% homologous to TGF-β1 (Derynck, et al. (1988) EMBO J 7:3737-3743). The structural characteristics of TGF-β1 as determined by nuclear magnetic resonance (Archer, et al. (1993) Biochemistry 32:1164-1171) agree with the crystal structure of TGF-β2 (Daopin, et al. (1992) Science 257:369-374; Schlunegger and Grutter (1992) Nature 358:430-434).

There are at least three different extracellular TGF-β receptors, Type I, II and III that are involved in the biological functions of TGF-β1, -β2 and -β3 (For reviews, see Derynck (1994) TIBS 19:548-553 and Massague (1990) Ann. Rev. Cell Biol. 6:597-641). The Type I and Type II receptors are transmembrane serine/threonine kinases, which in the presence of TGF-β form a heteromeric signaling complex (Wrana, et al (1992) Cell 71: 1003-1014).

The mechanism of activation of the heteromeric signaling complex at the cell surface has been elucidated (Wrana, et al. (1994) Nature 370: 341-347). TGF-β first binds the type II receptor that is a constitutively active transmembrane serine/threonine kinase. The type I receptor is subsequently recruited into the complex, phosphorylated at the GS domain and activated to phosphorylate downstream signaling components (e.g. Smad proteins) to initiate the intracellular signaling cascade. A constitutively active type I receptor (T204D mutant) has been shown to effectively transduce TGF-β responses, thus bypassing the requirement for TGF-β and the type II receptor (Wieser, et al. (1995) EMBO J 14: 2199-2208). Although no signaling function has been discovered for the type III receptor, it does increase TGF-β2's affinity for the type II receptor making it essentially equipotent with TGF-β1 and TGF-β3 (Lopez-Casillas, et al. (1993) Cell 73:1435-1444).

Vascular endothelial cells lack the Type III receptor. Instead endothelial cells express a structurally related protein called endoglin (Cheifetz, et al. (1992) J. Biol. Chem. 267: 19027-19030), which only binds TGF-β1 and TGF-β3 with high affinity. Thus, the relative potency of the TGF-β's reflects the type of receptors expressed in a cell and organ system. In addition to the regulation of the components in the multi-factorial signaling pathway, the distribution of the synthesis of TGF-β polypeptides also affects physiological function. The distribution of TGF-β2 and TGF-β3 is more limited (Derynck, et al. (1988) EMBO J 7:3737-3743) than TGF-β1, e.g., TGF-β3 is limited to tissues of mesenchymal origin, whereas TGF-β1 is present in both tissues of mesenchymal and epithelial origin.

TGF-β1 is a multifunctional cytokine critical for tissue repair. High concentrations of TGF-β1 are delivered to the site of injury by platelet granules (Assoian and Sporn (1986) J. Cell Biol. 102:1217-1223). TGF-β1 initiates a series of events that promote healing including chemo taxis of cells such as leukocytes, monocytes and fibroblasts, and regulation of growth factors and cytokines involved in angiogenesis, cell division associated with tissue repair and inflammatory responses. TGF-β1 also stimulates the synthesis of extracellular matrix components (Roberts, et al. (1986) Proc. Natl. Acad. Sci. USA 83:4167-4171; Sporn, et al. (1983) Science 219:1329-1330; Massague (1987) Cell 49:437-438) and most importantly for understanding the pathophysiology of TGF-β1, TGF-β1 autoregulates its own synthesis (Kim, et al. (1989) J. Biol. Chem. 264:7041-7045).

The compounds disclosed herein may also exhibit other kinase activity, such as p38 kinase inhibition and/or KDR (VEGFR2) kinase inhibition. Assays to determine such kinase activity are known in the art and one skilled in the art would be able to test the disclosed compounds for such activity.

SUMMARY OF THE INVENTION

The disclosed invention also relates to the select compound of Formula II:

Formula II

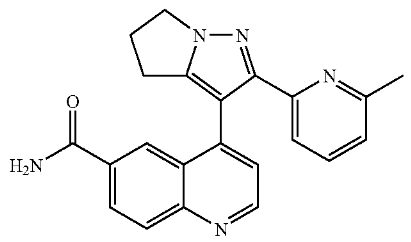

2-(6-methyl-pyridin-2-yl)-3-[6-amido-quinolin-4-yl)-5,6-dihydro-4H-pyrrolo[1,2-b]pyrazole and the pharmaceutically acceptable salts thereof.

The compound above is generically disclosed and claimed in PCT patent application PCT/US02/11884, filed 13 May 2002, which claims priority from U.S. patent application U.S. Ser. No. 60/293,464 , filed 24 May 2001, and incorporated herein by reference.

DETAILED DESCRIPTION OF THE INVENTION

The term "effective amount" as used in an "an effective amount of a compound of Formula I," for example, refers to an amount of a compound of the present invention that is capable of inhibiting TGF-beta.

The term μM refers to micromolar.

The general chemical terms used herein have their usual meanings.

The following abbreviations are used throughout the synthesis Schemes and Examples:

DMF refers to dimethyl formamide

THF refers to tetrahydrofuran

Ms refers to mesyl which is methylsulfonyl

THP refers to tetrahydropyran

The compounds disclosed herein can be made according to the following schemes and examples. The examples should in no way be understood to be limiting in any way as to how the compounds may be made.

The following scheme illustrates the preparation of the compound of Formula I.

Scheme I

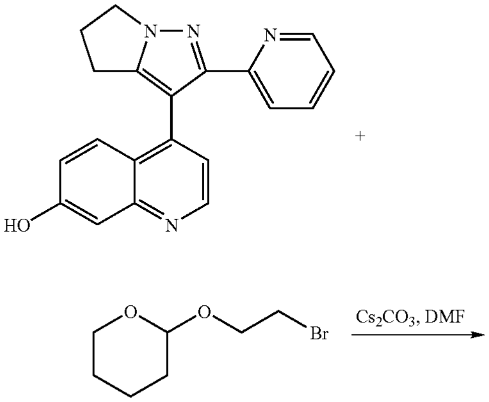

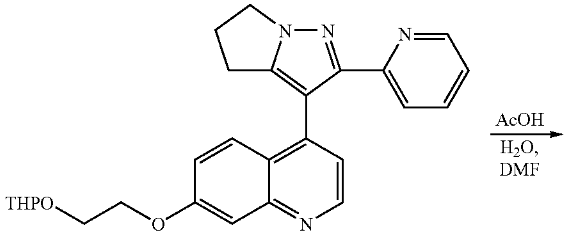

(A)

-continued

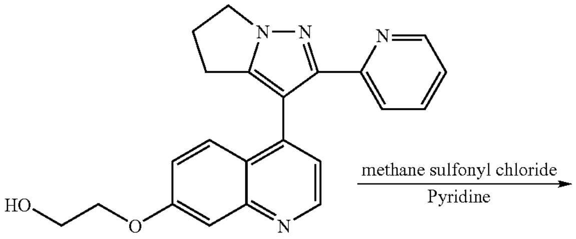

(B)

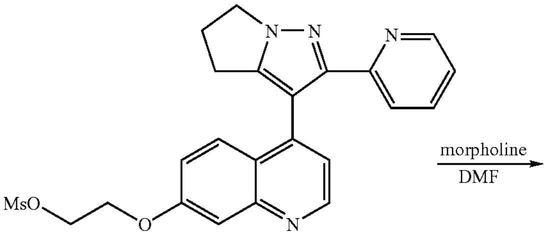

(C)

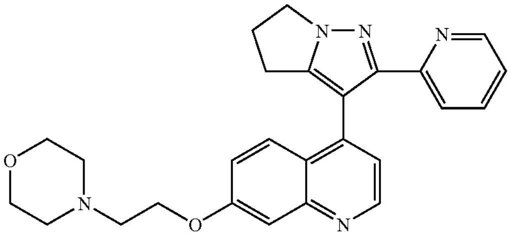

Formula I

The following scheme illustrates the preparation of the compound of Formula II.

Scheme II

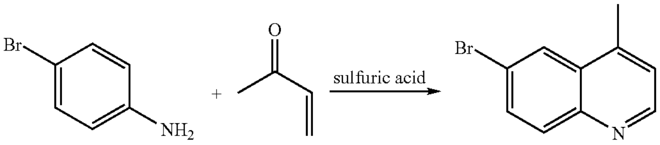

(A)

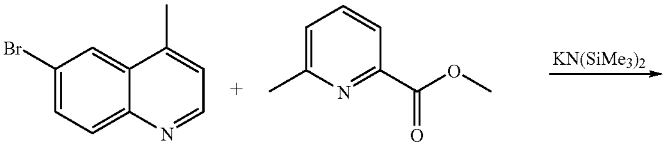

(B) (C)

-continued

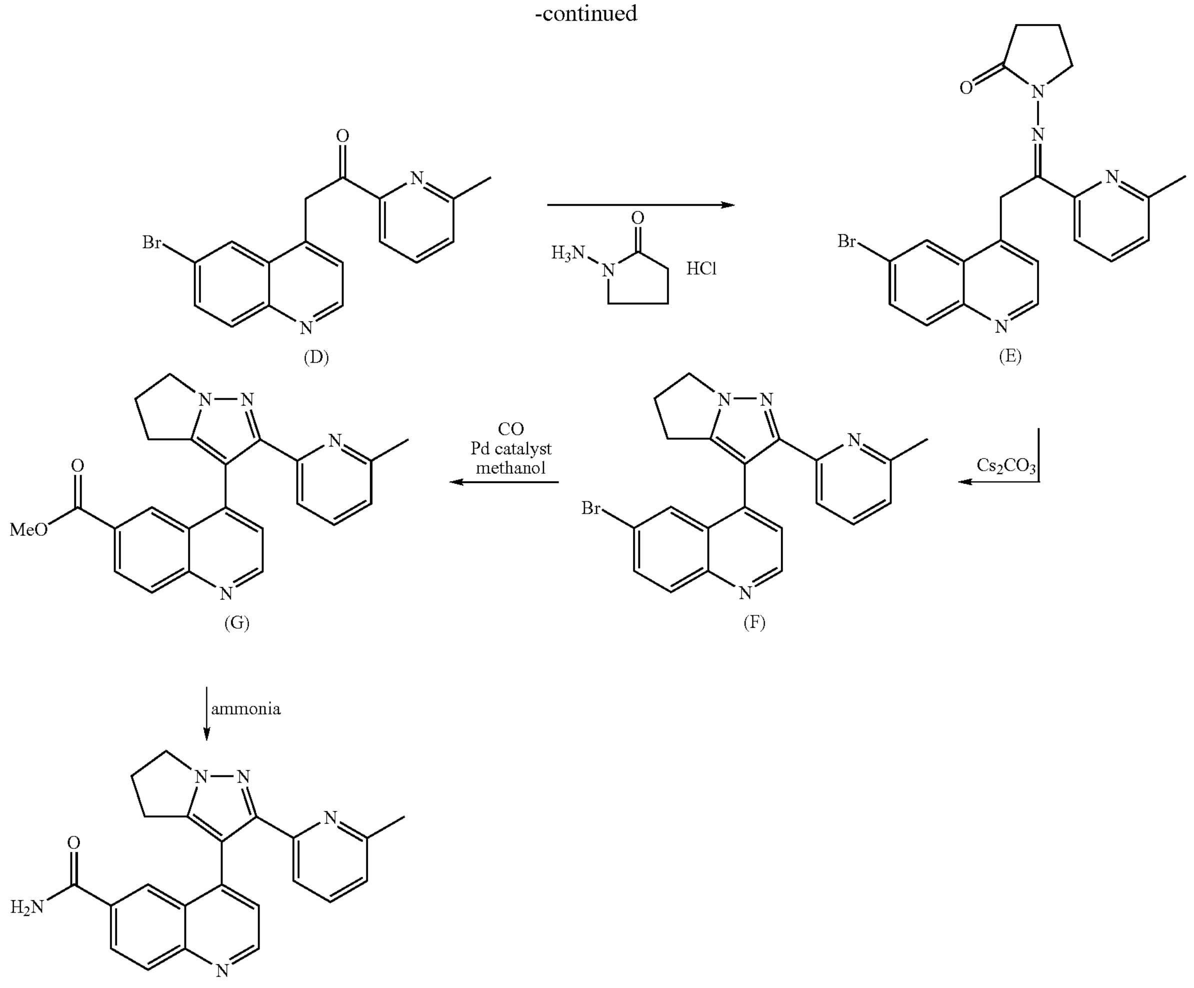

(D) (E) (G) (F)

Formula II

The following examples further illustrate the preparation of the compounds of this invention as shown schematically in Schemes I and II.

EXAMPLE 1

Preparation of 7-(2-morpholin-4-yl-ethoxy)-4-(2-pyridin-2-yl-5,6-dihydro-4H-pyrrolo[1,2-b]pyrazol-3-yl)-quinoline

A. Preparation of 4-(2-pyridin-2-yl-5,6-dihydro-4H-pyrrolo[1,2-b]pyrazol-3-yl)-7-[2-(tetrahydropyran-2-yloxy)ethoxy]quinoline Heat 4-(2-pyridin-2-yl-5,6-dihydro-4H-pyrrolo[1,2-b]pyrazol-3-yl)-quinolin-7-ol (376 mg, 1.146 mmol), cesium carbonate (826 mg, 2.54 mmol), and 2-(2-bromoethoxy)tetrahydro-2H-pyran (380 μL, 2.52 mmol) in DMF (5 mL) at 120° C. for 4 hours. Quench the reaction with saturated sodium chloride and then extract with chloroform. Dry the organic layer over sodium sulfate and concentrate in vacuo. Purify the reaction mixture on a silica gel column eluting with dichloromethane to 10% methanol in dichloromethane to give the desired subtitled intermediate as a yellow oil (424 mg, 81%). MS $ES^+$m/e 457.0 (M+1).

B. Preparation of 2-[4-(2-pyridin-2-yl-5,6-dihydro-4H-pyrrolo[1,2-b]pyrazol-3-yl)-quinolin-7-yloxy]-ethanol Heat a solution of 4-(2-pyridin-2-yl-5,6-dihydro-4H-pyrrolo[1,2-b]pyrazol-3-yl)-7-[2-(tetrahydropyran-2-yloxy)ethoxy]quinoline (421 mg, 0.92 mmol) in acetic acid:tetrahydrofuran:water (4:2:1) (20 mL). Remove the solvent in vacuo and recover the residue with chloroform:isopropyl (3:1). Wash the organic layer with saturated sodium bicarbonate and dry over sodium sulfate. Concentrate in vacuo. The residue will be pure enough for the next step in the scheme (425 mg, 100%). MS $ES^+$ m/e 373.1 (M+1).

C. Preparation of methanesulfonic acid 2-[4-(2-pyridin-2-yl-5,6-dihydro-4H-pyrrolo[1,2-b]pyrazol-3-yl)-quinolin-7-yloxy]-ethyl ester Stir a solution of 2-[4-(2-pyridin-2-yl-5,6-dihydro-4H-pyrrolo[1,2-b]pyrazol-3-yl)-quinolin-7-yloxy]-ethanol (293 mg, 0.78 mmol) and methane sulfonyl chloride (68 μL, 0.81 ml) in dried pyridine (5 mL) for 2 hours. Remove the pyridine in vacuo and recover the residue with chloroform. Wash the organic layer with saturated sodium bicarbonate and dry over sodium sulfate to give the desired subtitled intermediate as a white foam (425 mg, 100%). MS ES$^+$ m/e 451.1 (M+1).

D. Preparation of 7-(2-morpholin-4-yl-ethoxy)-4-(2-pyridin-2-yl-5,6-dihydro-4H-pyrrole[1,2-b]pyrazol-3-yl)-quinoline

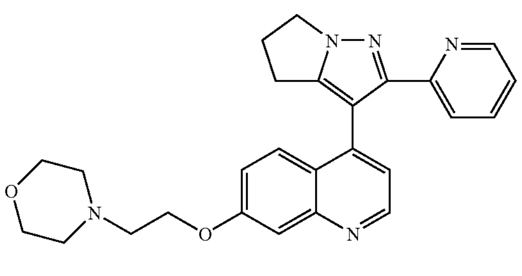

Heat methanesulfonic acid 2-[4-(2-pyridin-2-yl-5,6-dihydro-4H-pyrrolo[1,2-b]pyrazol-3-yl)-quinolin-7-yloxy]-ethyl ester (87 mg, 0.19 mmol) with morpholine (1 mL) at 50° C. for 4 hours. Remove the morpholine in vacuo and then extract the product with isopropyl alcohol chloroform (1:3). Wash the organic layer with sodium chloride and dry over sodium sulfate. Concentrate in vacuo to give the desired title product as a slight yellow solid (83 mg, 100%). MS ES$^+$ m/e 442.0 (M+1).

EXAMPLE 2

Preparation of 2-(6-methyl-pyridin-2-yl)-3-[6-amide-quinolin-4-yl)-5,6-dihydro-4H-pyrrolo[1,2-b]pyrazole A. Preparation of 6-bromo-4-methyl-quinoline Stir a solution of 4-bromo-phenylamine (1 eq), in 1,4-dioxane and cool to approximately 12° C. Slowly add sulfuric acid (2 eq) and heat at reflux. Add methylvinyl ketone (1.5 eq) dropwise into the refluxing solution. Heat the solution for 1 hour after addition is complete. Evaporate the reaction solution to dryness and dissolve in methylene chloride. Adjust the solution to pH 8 with 1 M sodium carbonate and extract three times with water. Chromatograph the residue on $SiO_2$ (70/30 hexane/ethyl acetate) to obtain the desired subtitled intermediate. MS ES+m/e=158.2 (M+1).

B. Preparation of 6-methyl-pyridine-2-carboxylic acid methyl ester

Suspend 6-methyl-pyridine-2-carboxylic acid (10 g, 72.9 mmol) in methylene chloride (200 mL). Cool to 0° C. Add methanol (10 mL), 4-dimethylaminopyridine (11.6 g, 94.8 mmol), and 1-(3-dimethylaminopropyl)-3-ethylcarbodiimide hydrochloride (EDC) (18.2 g, 94.8 mmol). Stir the mixture at room temperature for 6 hours, wash with water and brine, and dry over sodium sulfate. Filter the mixture and concentrate in vacuo. Chromatograph the residue on $SiO_2$ (50% ethyl acetate/hexanes) to obtain the desired subtitled intermediate, 9.66 g (92%), as a colorless liquid. $^1$H NMR ($CDCl_3$) δ 7.93-7.88 (m, 1H), 7.75-7.7 (m, 1H), 7.35-7.3 (m, 1H), 4.00 (s, 3H), 2.60 (s, 3H).

C. Preparation of 2-(6-bromo-quinolin-4-yl)-1-(6-methyl-pyridin-2-yl)-ethanone

Dissolve 6-bromo-4-methyl-quinoline (38.5 g, 153 mmol) in 600 mL dry THF. Cool to −70° C. and treat with the dropwise addition of 0.5 M potassium hexamethyldisilazane ($KN(SiMe_3)_2$ (400 mL, 200 mmol) over 2 hours while keeping the temperature below −65° C. Stir the resultant solution at −70° C. for 1 hour and add a solution of 6-methylpyridine-2-carboxylic acid methyl ester (27.2, 180 mmol) in 100 mL dry THF dropwise over 15 minutes. During the addition, the mixture will turn from dark red to pea-green and form a precipitate. Stir the mixture at −70° C. over 2 hours then allow it to warm to ambient temperature with stirring for 5 hours. Cool the mixture then quench with 12 N HCl to pH=1. Raise the pH to 9 with solid potassium carbonate. Decant the solution from the solids and extract twice with 200 mL ethyl acetate. Combine the organic extracts, wash with water and dry over potassium carbonate. Stir the solids in 200 mL water and 200 mL ethyl acetate and treat with additional potassium carbonate. Separate the organic portion and dry with the previous ethyl acetate extracts. Concentrate the solution in vacuo to a dark oil. Pass the oil through a 300 mL silica plug with methylene chloride then ethyl acetate. Combine the appropriate fractions and concentrate in vacuo to yield an amber oil. Rinse the oil down the sides of the flask with methylene chloride then dilute with hexane while swirling the flask to yield 38.5 g (73.8%) of the desired subtitled intermediate as a yellow solid. MS ES+=341 (M+1).

D. Preparation of 1-[2-(6-bromo-quinolin-4-yl)-1-(6-methyl-pyridin-2-yl)-ethylideneamino]-pyrrolidin-2-one Stir a mixture of 2-(6-bromo-quinolin-4-yl)-1-(6-methyl-pyridin-2-yl)-ethanone (38.5 g, 113 mmol) and 1-aminopyrrolidinone hydrochloride (20 g, 147 mmol) in 115 mL pyridine at ambient temperature for 10 hours. Add about 50 g of 4 Å unactivated sieves. Continue stirring an additional 13 h and add 10-15 g silica and filter the mixture through a 50 g silica plug. Elute the silica plug with 3 L ethyl acetate. Combine the filtrates and concentrate in vacuo. Collect the hydrazone precipitate by filtration and suction dry to yield 33.3 g (69.7%) of the desired subtitled intermediate as an off-white solid. MS ES$^+$=423 (M+1).

E. Preparation of 6-bromo-4-[2-(6-methyl-pyridin-2-yl)-5,6-dihydro-4H-pyrrolo[1,2-b]pyrazol-3-yl]-quinoline To a mixture of (1.2 eq.) cesium carbonate and 1-[2-(6-bromo-quinolin-4-yl)-1-(6-methyl-pyridin-2-yl)-ethylideneamino]-pyrrolidin-2-one (33.3 g, 78.7 mmol) add 300 mL dry N,N-dimethylformamide. Stir the mixture 20 hours at 100° C. The mixture may turn dark during the reaction. Remove the N,N-dimethylformamide in vacuo. Partition the residue between water and methylene chloride. Extract the aqueous portion with additional methylene chloride. Filter the organic solutions through a 300 mL silica plug, eluting with 1.5 L methylene chloride, 1.5 L ethyl acetate and 1.5 L acetone. Combine the appropriate fractions and concentrate in vacuo. Collect the resulting precipitate by filtration to yield 22.7 g (71.2%) of the desired subtitled intermediate as an off-white solid. MS ES$^+$=405 (M+1).

F. Preparation of 4-[2-(6-methyl-pyridin-2-yl)-5,6-dihydro-4H-pyrrolo[1,2-b]pyrazol-3-yl]-quinoline-6-carboxylic acid methyl ester Add 6-bromo-4-[2-(6-methyl-pyridin-2-yl)-5,6-dihydro-4H-pyrrolo[1,2-b]pyrazol-3-yl]-quinoline (22.7 g, 45 mmol) to a mixture of sodium acetate (19 g, 230 mmol) and the palladium catalyst [1,1'-bis(diphenylphosphino)ferrocene] dichloropalladium(II), complex with dichloromethane (1:1) (850 mg, 1.04 mmol) in 130 mL methanol. Place the mixture under 50 psi carbon monoxide atmosphere and stir while warming to 90° C. over 1 hour and with constant charging with additional carbon monoxide. Allow the mixture to cool over 8 hours, recharge again with carbon monoxide and heat to 90° C. The pressure may rise to about 75 PSI. The reaction is complete in about an hour when the pressure is stable and the (1:1 toluene/acetone) shows no remaining bromide. Partition the mixture between methylene chloride (600 mL) and water (1 L). Extract the aqueous portion with an additional portion of methylene chloride (400 mL). Filter the organic solution through a 300 mL silica plug and wash with 500 mL methylene chloride, 1200 mL ethyl acetate and 1500 mL acetone. Discard the acetone portion. Combine appropriate fractions and concentrate to yield 18.8 g (87.4%) of the desired subtitled intermediate as a pink powder. MS $ES^+$=385 (M+1).

G. Preparation of 2-(6-methyl-pyridin-2-yl)-3-[6-amido-quinolin-4-yl)-5,6-dihydro-4H-pyrrolo[1,2-b]pyrazole

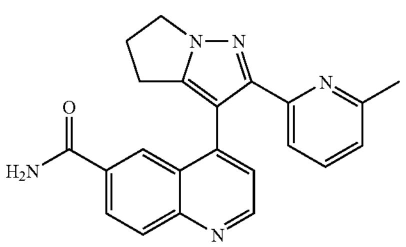

Warm a mixture of 4-[2-(6-methyl-pyridin-2-yl)-5,6-dihydro-4H-pyrrolo[1,2-b]pyrazol-3-yl]-quinoline-6-carboxylic acid methyl ester in 60 mL 7 N ammonia in methanol to 90° C. in a stainless steel pressure vessel for 66 hours. The pressure will rise to about 80 PSI. Maintain the pressure for the duration of the reaction. Cool the vessel and concentrate the brown mixture in vacuo. Purify the residual solid on two 12 g Redi-Pak cartridges coupled in series eluting with acetone. Combine appropriate fractions and concentrate in vacuo. Suspend the resulting nearly white solid in methylene chloride, dilute with hexane, and filter. The collected off-white solid yields 1.104 g (63.8%) of the desired title product. MS $ES^+$=370 (M+1).

The compounds disclosed herein were tested by the following protocols for TGF-β inhibition, as described below in the protocol description.

TGF-β Receptor I Purification and In Vitro Kinase Reactions

For TGF-β Type I (RIT204D) Receptors:

The 6×-HIS tagged cytoplasmic kinase domain of each receptor was expressed and purified from Sf9 insect cell lysates as briefly described below:

Cell pellets after 48-72 hours of infection were lysed in lysis buffer (LB: 50 mM Tris pH 7.5, 150 mM NaCl, 50 mM NaF, 0.5% NP40 with freshly added 20 mM β-mercaptoethanol, 10 mM imidazole, 1 mM PMSF, 1×EDTA-free Complete Protease Inhibitor (Boehringer Mannheim).

Cell lysates were clarified by centrifugation and 0.45 uM filtered prior to purification by Ni/NTA affinity chromatography (Qiagen).

Chromatography Protocol:

Equilibrate with 10 CV of LB, load sample, wash with 10 CV RIPA buffer (50 mM Tris pH 7.5, 150 mM NaCl, 1% NP40, 1 mM EDTA, 0.25% sodium deoxycholate, added fresh 20 mM β-mercaptoethanol, 1 mM PMSF), wash with 10 CV LB, wash with 10 CV 1×KB (50 mM Tris pH 7.5, 150 mM NaCl, 4 mM $MgCl_2$, 1 mM NaF, 2 mM β-mercaptoethanol), elute with a linear gradient of 1×KB containing 200 mM imidazole.

Both enzymes were approximately 90% pure and had autophosphorylation activity.

Reactions: 170-200 nM enzyme in 1×KB, compound dilution series in 1×KB/16% DMSO (20 μM to 1 nM final concentration with 4% DMSO final concentration), reactions started by adding ATP mix (4 μM ATP/1 μCi $^{33}$P-γ-ATP final concentrations) in 1×KB.

Reactions were incubated at 30° C. for 1 hour. Reactions were stopped and quantitated using standard TCA/BSA precipitation onto Millipore FB glass fiber filter plates and by liquid scintillation counting on a MicroBeta JET.

The compounds disclosed herein inhibit the TGF-β Type I (RIT204D) receptor kinase domain with $IC_{50}$ values <20 μM, while exhibiting less toxicity in vivo than structurally related compounds as disclosed in PCT patent application PCT/US02/11884 identified above.

Conditions "characterized by enhanced TGF-β activity" include those wherein TGF-β synthesis is stimulated so that TGF-β is present at increased levels or wherein TGF-β latent protein is undesirably activated or converted to active TGF-β protein or wherein TGF-β receptors are upregulated or wherein the TGF-β protein shows enhanced binding to cells or extracellular matrix in the location of the disease. Thus, in either case "enhanced activity" refers to any condition wherein the biological activity of TGF-β is undesirably high, regardless of the cause.

A number of diseases have been associated with TGF-β1 over production. Inhibitors of TGF-β intracellular signaling pathway are useful treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN, and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, scleroderma, dermatomyositis, eosinophilic fascitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma, chemical contact, or allergies. Another autoimmune disorder associated with fibroproliferative characteristics is rheumatoid arthritis.

Eye diseases associated with a fibroproliferative condition include retinal reattachment surgery accompanying proliferative vitreoretinopathy, cataract extraction with intraocular lens implantation, and post glaucoma drainage surgery are associated with TGF-β1 overproduction.

Fibrotic diseases associated with TGF-β1 overproduction can be divided into chronic conditions such as fibrosis of the kidney, lung and liver and more acute conditions such as dermal scarring and restenosis (Chamberlain, J. Cardiovascular Drug Reviews, 19(4):329-344). Synthesis and secretion of TGF-β1 by tumor cells can also lead to immune suppression such as seen in patients with aggressive brain or breast tumors (Arteaga, et al. (1993) J. Clin. Invest. 92:2569-2576). The course of Leishmanial infection in mice is drastically altered by TGF-β1 (Barral-Netto, et al. (1992) Science 257: 545-547). TGF-β1 exacerbated the disease, whereas TGF-β1 antibodies halted the progression of the disease in genetically susceptible mice. Genetically resistant mice became susceptible to Leishmanial infection upon administration of TGF-β1.

The profound effects of TGF-β1 on extracellular matrix deposition have been reviewed (Rocco and Ziyadeh (1991) in Contemporary Issues in Nephrology v. 23, Hormones, autocoids and the kidney. ed. Jay Stein, Churchill Livingston, N.Y. pp. 391-410; Roberts, et al. (1988) Rec. Prog. Hormone Res. 44:157-197) and include the stimulation of the synthesis and the inhibition of degradation of extracellular matrix components. Since the structure and filtration properties of the glomerulus are largely determined by the extracellular matrix composition of the mesangium and glomerular membrane, it is not surprising that TGF-β1 has profound effects on the kidney. The accumulation of mesangial matrix in proliferative glomerulonephritis (Border, et al. (1990) Kidney Int. 37:689-695) and diabetic nephropathy (Mauer, et al. (1984) J. Clin. Invest. 74:1143-1155) are clear and dominant pathological features of the diseases. TGF-β1 levels are elevated in human diabetic glomerulosclerosis (advanced neuropathy) (Yamamoto, et al. (1993) Proc. Natl. Acad. Sci. 90:1814-1818). TGF-β1 is an important mediator in the genesis of renal fibrosis in a number of animal models (Phan, et al. (1990) Kidney Int. 37:426; Okuda, et al. (1990) J. Clin. Invest. 86:453). Suppression of experimentally induced glomerulonephritis in rats has been demonstrated by antiserum against TGF-β1 (Border, et al. (1990) Nature 346:371) and by an extracellular matrix protein, decorin, which can bind TGF-β1 (Border, et al. (1992) Nature 360:361-363).

Too much TGF-β1 leads to dermal scar-tissue formation. Neutralizing TGF-β1 antibodies injected into the margins of healing wounds in rats have been shown to inhibit scarring without interfering with the rate of wound healing or the tensile strength of the wound (Shah, et al. (1992) Lancet 339:213-214). At the same time there was reduced angiogenesis, reduced number of macrophages and monocytes in the wound, and a reduced amount of disorganized collagen fiber deposition in the scar tissue.

TGF-β1 may be a factor in the progressive thickening of the arterial wall which results from the proliferation of smooth muscle cells and deposition of extracellular matrix in the artery after balloon angioplasty. The diameter of the restenosed artery may be reduced 90% by this thickening, and since most of the reduction in diameter is due to extracellular matrix rather than smooth muscle cell bodies, it may be possible to open these vessels to 50% simply by reducing extensive extracellular matrix deposition. In uninjured pig arteries transfected in vivo with a TGF-β1 gene, TGF-β1 gene expression was associated with both extracellular matrix synthesis and hyperplasia (Nabel, et al. (1993) Proc. Natl. Acad. Sci. USA 90:10759-10763). The TGF-β1 induced hyperplasia was not as extensive as that induced with PDGF-BB, but the extracellular matrix was more extensive with TGF-β1 transfectants. No extracellular matrix deposition was associated with FGF-1 (a secreted form of FGF) induced hyperplasia in this gene transfer pig model (Nabel (1993) Nature 362:844-846).

There are several types of cancer where TGF-β1 produced by the tumor may be deleterions. MATLyLu rat prostate cancer cells (Steiner and Barrack (1992) Mol. Endocrinol 6:15-25) and MCF-7 human breast cancer cells (Arteaga, et al. (1993) Cell Growth and Differ. 4:193-201) became more tumorigenic and metastatic after transfection with a vector expressing the mouse TGF-β1. TGF-β1 has been associated with angiogenesis, metastasis and poor prognosis in human prostate and advanced gastric cancer (Wikstrom, P., et al. (1998) Prostate 37: 19-29; Saito, H. et al. (1999) Cancer 86: 1455-1462). In breast cancer, poor prognosis is associated with elevated TGF-β (Dickson, et al. (1987) Proc. Natl. Acad. Sci. USA 84:837-841; Kasid, et al. (1987) Cancer Res. 47:5733-5738; Daly, et al. (1990) J. Cell Biochem. 43:199-211; Barrett-Lee, et al. (1990) Br. J Cancer 61:612-617; King, et al. (1989) J. Steroid Biochem. 34:133-138; Welch, et al. (1990) Proc. Natl. Acad. Sci. USA 87:7678-7682; Walker, et al. (1992) Eur. J. Cancer 238:641-644) and induction of TGF-β1 by tamoxifen treatment (Butta, et al. (1992) Cancer Res. 52:4261-4264) has been associated with failure of tamoxifen treatment for breast cancer (Thompson, et al. (1991) Br. J. Cancer 63:609-614). Anti TGF-β1 antibodies inhibit the growth of MDA-231 human breast cancer cells in athymic mice (Arteaga, et al. (1993) J. Clin. Invest. 92:2569-2576), a treatment which is correlated with an increase in spleen natural killer cell activity. CHO cells transfected with latent TGF-β1 also showed decreased NK activity and increased tumor growth in nude mice (Wallick, et al. (1990) J. Exp. Med. 172:1777-1784). Thus, TGF-β secreted by breast tumors may cause an endocrine immune suppression. High plasma concentrations of TGF-β1 have been shown to indicate poor prognosis for advanced breast cancer patients (Anscher, et al. (1993) N. Engl. J. Med. 328:1592-1598). Patients with high circulating TGF-β before high dose chemotherapy and autologous bone marrow transplantation are at high risk for hepatic veno-occlusive disease (15-50% of all patients with a mortality rate up to 50%) and idiopathic interstitial pneumonitis (40-60% of all patients). The implication of these findings is 1) that elevated plasma levels of TGF-β1 can be used to identify at risk patients and 2) that reduction of TGF-β1 could decrease the morbidity and mortality of these common treatments for breast cancer patients.

Many malignant cells secrete transforming growth factor-β (TGF-β), a potent immunosuppressant, suggesting that TGF-β production may represent a significant tumor escape mechanism from host immunosurveillance. Establishment of a leukocyte subpopulation with disrupted TGF-β signaling in the tumor-bearing host offers a potential means for immunotherapy of cancer. A transgenic animal model with disrupted TGF-β signaling in T cells is capable of eradicating a normally lethal TGF-β over expressing lymphoma tumor, EL4 (Gorelik and Flavell, (2001) Nature Medicine 7(10): 1118-1122). Down regulation of TGF-β secretion in tumor cells results in restoration of immunogenicity in the host, while T-cell insensitivity to TGF-β results in accelerated differentiation and autoimmunity, elements of which may be required in order to combat self-antigen-expressing tumors in a tolerized host. The immunosuppressive effects of TGF-β have also been implicated in a subpopulation of HIV patients with lower than predicted immune response based on their CD4/CD8 T cell counts (Garba, et al. J. Immunology (2002) 168: 2247-2254). A TGF-β neutralizing antibody was capable of reversing the effect in culture, indicating that TGF-β signaling inhibitors may have utility in reversing the immune suppression present in this subset of HIV patients.

During the earliest stages of carcinogenesis, TGF-β1 can act as a potent tumor suppressor and may mediate the actions of some chemopreventive agents. However, at some point during the development and progression of malignant neoplasms, tumor cells appear to escape from TGF-β-dependent growth inhibition in parallel with the appearance of bioactive TGF-β in the microenvironment. The dual tumor suppression/tumor promotion roles of TGF-β have been most clearly elucidated in a transgenic system over expressing TGF-β in keratinocytes. While the transgenics were more resistant to formation of benign skin lesions, the rate of metastatic conversion in the transgenics was dramatically increased (Cui, et al (1996) Cell 86(4):531-42). The production of TGF-β1 by malignant cells in primary tumors appears to increase with advancing stages of tumor progression. Studies in many of the major epithelial cancers suggest that the increased production of TGF-β by human cancers occurs as a relatively late event during tumor progression. Further, this tumor-associated TGF-β provides the tumor cells with a selective advantage and promotes tumor progression. The effects of TGF-β on cell/cell and cell/stroma interactions result in a greater propensity for invasion and metastasis. Tumor-associated TGF-β may allow tumor cells to escape from immune surveillance since it is a potent inhibitor of the clonal expansion of activated lymphocytes. TGF-β has also been shown to inhibit the production of angiostatin. Cancer therapeutic modalities such as radiation therapy and chemotherapy induce the production of activated TGF-β in the tumor, thereby selecting outgrowth of malignant cells that are resistant to TGF-β growth inhibitory effects. Thus, these anticancer treatments increase the risk and hasten the development of tumors with enhanced growth and invasiveness. In this situation, agents targeting TGF-β-mediated signal transduction might be a very effective therapeutic strategy. The resistance of tumor cells to TGF-β has been shown to negate much of the cytotoxic effects of radiation therapy and chemotherapy and the treatment-dependent activation of TGF-β in the stroma may even be detrimental as it can make the microenvironment more conductive to tumor progression and contributes to tissue damage leading to fibrosis. The development of a TGF-β signal transduction inhibitors is likely to benefit the treatment of progressed cancer alone and in combination with other therapies.

The compounds are useful for the treatment of cancer and other disease states influenced by TGF-β by inhibiting TGF-β in a patient in need thereof by administering said compound(s) to said patient. TGF-β would also be useful against atherosclerosis (T. A. McCaffrey: TGF-βs and TGF-β Receptors in Atherosclerosis: Cytokine and Growth Factor Reviews 2000, 11, 103-114) and Alzheimer's (Masliah, E.; Ho, G; Wyss-Coray, T.: Functional Role of TGF-β in Alzheimer's Disease Microvascular Injury: Lessons from Transgenic Mice: Neurochemistry International 2001, 39, 393-400) diseases.

Pharmaceutical Compositions

The compositions of the present invention are therapeutically effective amounts of the TGF-β antagonists, noted above. The composition may be formulated with common excipients, diluents or carriers, and compressed into tablets, or formulated elixirs or solutions for convenient oral administration or administered by intramuscular intravenous routes. The compounds can be administered transdermally and maybe formulated as sustained release dosage forms and the like.

The method of treating a human patient according to the present invention includes administration of the TGF-β antagonists. The TGF-β antagonists are formulated into formulations which may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) the compounds. Dosages from about 0.5 to about 300 mg/kg per day, preferably 0.5 to 20 mg/kg, of active ingredient may be administered although it will, of course, readily be understood that the amount of the compound actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations useful for separate administration of the TGF-β antagonists will normally consist of at least one compound selected from the compounds specified herein mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, for injection, and for oral ingestion.

We claim:

1. A method of treating prostate cancer which comprises administering to a patient in need thereof a therapeutically effective amount of 2-(6-methyl-pyridin-2-yl)-3-[6-amido-quinolin-4-yl)-5,6-dihydro-4H-pyrrolo[1,2-b]pyrazole or a pharmaceutically acceptable salt thereof.

* * * * *